United States Patent
Honda

(10) Patent No.: US 6,332,015 B1
(45) Date of Patent: Dec. 18, 2001

(54) RADIOGRAPHIC DIAGNOSIS APPARATUS, RADIOGRAPHIC DIAGNOSIS METHOD, PLATE MEMBER, AND POSITION DETECTING METHOD

(75) Inventor: Michitaka Honda, Yaita (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/441,056

(22) Filed: Nov. 16, 1999

(30) Foreign Application Priority Data

Nov. 17, 1998 (JP) .................................................. 10-326993

(51) Int. Cl.[7] ....................................................... A61B 6/00

(52) U.S. Cl. ...................... 378/98.11; 378/98.8; 378/98.9

(58) Field of Search ............................... 378/98.11, 98.8, 378/98.9, 98.2

(56) References Cited

U.S. PATENT DOCUMENTS 5,864,146 * 1/1999 Karellas .............................. 378/98.8

OTHER PUBLICATIONS

William R. Brody, et al., "A Method for Selective Tissue and Bone Visualization Using Dual Energy Scanned Projection Radiography", Med. Phys. vol. 8, No. 3, May/Jun. 1981, pp. 353–357.

* cited by examiner

Primary Examiner—Drew Dunn
(74) Attorney, Agent, or Firm—Oblon, Spivak, McClelland, Maier & Neustadt, P.C.

(57) ABSTRACT

A radiographic diagnosis apparatus includes an X-ray generation device for irradiating an object with X-rays, a two-dimensional array detector which is formed by arraying small detecting elements in a two-dimensional matrix and opposing the X-ray generation device with the object interposed between them and detects X-rays transmitted through the object in units of pixels, a ray conversion plate adhered to the detecting surface of the array detector to change the properties of X-rays in units of pixels, and an image processor for performing image processing based on data from the array detector, thereby generating a radiographic diagnosis image. The ray conversion plate includes a plurality of different types of attenuating elements arrayed in a checkerboard pattern to attenuate radiation at different attenuation ratios. The properties of X-rays are changed via the ray conversion plate. The ray conversion plate changes the properties into two types. The array detector detects two types of property-changed X-ray signals transmitted through the object in units of pixels, and converts the signals into digital signals.

24 Claims, 5 Drawing Sheets

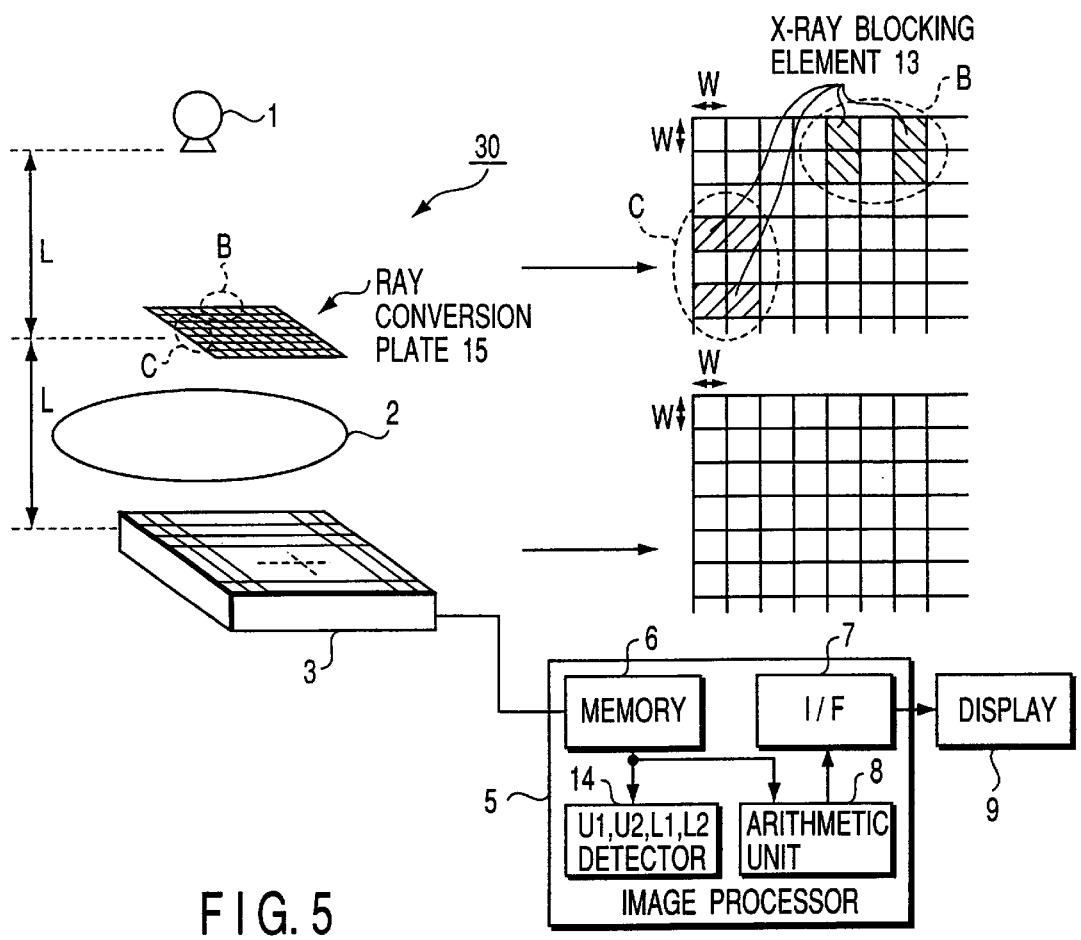
F I G. 5
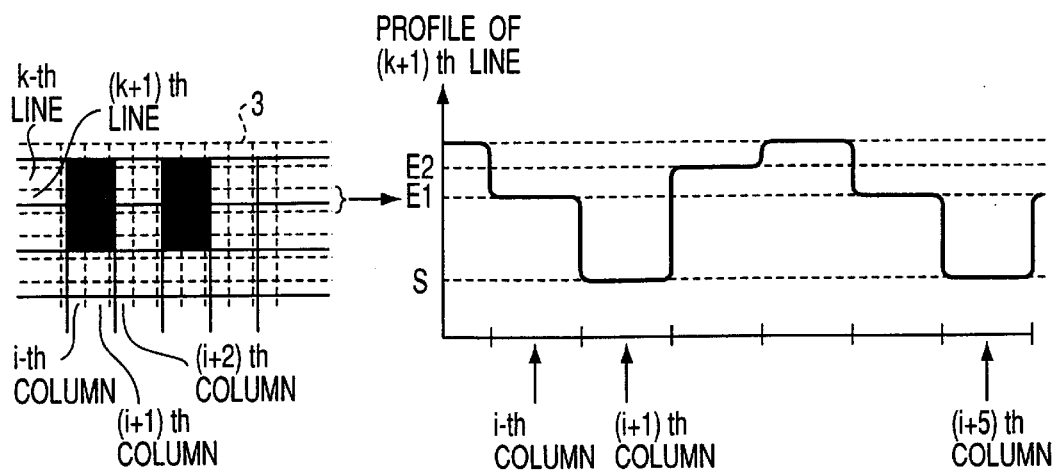
F I G. 6

RADIOGRAPHIC DIAGNOSIS APPARATUS, RADIOGRAPHIC DIAGNOSIS METHOD, PLATE MEMBER, AND POSITION DETECTING METHOD

BACKGROUND OF THE INVENTION

The present invention relates to a radiographic diagnosis apparatus which irradiates an object with radiation such as X-rays from a radiation source and generates a radiographic diagnosis image by detecting the radiation transmitted through the object and, more particularly, to a radiographic diagnosis apparatus which uses a two-dimensional array detector, in which a plurality of detecting elements are arrayed in a two-dimensional matrix, as a radiation detector, irradiates an object with a plurality of radiations differing in energy, and reconstructs a desired image by using the energy differences.

This application is based on Japanese Patent Application No. 10-326993, filed Nov. 17, 1998, the entire content of which is incorporated herein by reference.

One conventional radiographic diagnosis apparatus using radiation such as X-rays is a technique which acquires images by using two different X-ray energies (high and low energies) and performs energy subtraction by linear arithmetic operations (weighted differential processing) for the images (William R. Brody et. al., "A method for selective tissue and bone visualization using dual energy scanned projection radiography", Med. Phys. 8(3), May/June 1981). The purpose of this technique is to display only a soft tissue by erasing information, such as a bone, unnecessary for diagnosis by subtraction and to thereby allow easy diagnosis of a soft tissue hidden behind a bone.

Also, a technique by which images are acquired by a plurality of different X-ray energies, not by two different energies, and the energy absorption characteristic of a substance is visualized by linear arithmetic operations for the images is described in Japanese Patent Application No. 3-334788 assigned to the same assignee as the application concerned. The purpose of this technique is to visualize the differences between X-ray energy spectrum absorbed by, e.g., bones, soft tissues, and lungs. Since the method of display is different from the one that displays X-ray attenuation amounts, the method is expected to be applied to tissue characterization.

As a means for acquiring a plurality of different energy images, a method of acquiring images by emitting a plurality of different radiations at different timings is known. This method sequentially emits a plurality of different radiations and acquires a plurality of image data by detecting the emitted radiations by a single detector. In this method, the same object is irradiated at least twice at different timings with different radiations. Therefore, if the object moves, the data acquisition positions of the second and subsequent radiations deviate from that of the first radiation. This generates an artifact and thereby degrades the image quality.

To prevent this, methods are being developed by which a plurality of different radiations are simultaneously emitted and detected by a plurality of different detectors. One example is a method which uses a detecting device formed by overlapping a plurality of detectors with a substance which changes X-ray properties sandwiched between them. This method emits one type of radiation, changes the radiation properties by passing it through the substance, and acquires a plurality of images at the same time by the first detector and the second and subsequent detectors. Since a plurality of different radiations are simultaneously emitted and a plurality of images are simultaneously acquired, no such artifact as caused by the motion of an object as described above is produced. However, a detector (first detector) placed nearest to an X-ray generator must transmit X-rays to a certain degree to a subsequent detector (second detector), i.e., must not absorb X-rays 100%. Also, the second detector detects X-rays attenuated by the first detector, so the incident dose is reduced compared to that to the first detector. As a consequence, the dose detected by each detector reduces, and this decreases the ratio of the effective dose to noise, i.e., the S/N ratio of an image; the influence of noise increases to degrade the image quality. Furthermore, since the detectors overlap each other in the form of a sandwich, scattering rays generated by the individual detectors have influence on each other. This degrades the image quality acquired by each detector.

An array detector in which small detecting elements are arrayed in a two-dimensional matrix has been developed recently as an X-ray detector (e.g., U.S. Pat. No. 4,672,454). This detector is characterized in that the positions of pixels corresponding to the pixels of a digital image are spatially determined. Feasibility of applying the aforementioned diagnosis methods such as energy subtraction to a detector having this two-dimensional array structure is under consideration.

This X-ray array detector, however, has a structure in which detecting elements are arrayed on the detector. Hence, it is necessary to lay in electric wires, for propagating input control signals to the detecting elements and output electrical signals from the detecting elements, inside the detector. If this detector is constructed into the shape of a sandwich, therefore, the shadow of the wiring in the first detecting element is projected onto the second detecting element to generate an artifact. This makes this detector difficult to put into practice.

As described above, no conventional means exists which acquires a plurality of different energy images without generating any artifact, reducing the S/N ratio, and degrading the image quality by scattering rays.

BRIEF SUMMARY OF THE INVENTION

Accordingly, it is an object of the present invention to provide a radiographic diagnosis apparatus which uses a two-dimensional array detector, acquires an image of an object by using radiations differing in energy, and prevents an artifact being caused by the motion of the object, or by the shadow of an internal structure of the detector, without deteriorating the S/N ratio.

According to the present invention, there is provided a radiographic diagnosis apparatus comprising a radiation source for irradiating an object with radiation, a detector comprising a plurality of detecting elements for detecting the radiation generated by the radiation source and transmitted through the object, and a ray conversion member placed between the radiation source and the detector and comprising a plurality of different types of attenuating elements for attenuating radiation at different attenuation ratios, wherein radiations differing in energy attenuated by the plurality of different types of attenuating elements are detected by the detecting elements respectively corresponding to the attenuating elements, thereby acquiring radiation images differing in energy.

In the present invention, it is possible to irradiate the detector with a plurality of different radiations and acquire a plurality of different images at once. Accordingly, it is possible to prevent an artifact caused by the motion of an object, or by the shadow of an internal structure of a detector, without deteriorating the S/N ratio.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 5 is a view schematically showing the overall structure of the third embodiment of a radiographic diagnosis apparatus according to the present invention;

FIG. 6 shows a method of detecting the positional deviation between a ray conversion plate and an array detector in the radiographic diagnosis apparatus according to the third embodiment;

DETAILED DESCRIPTION OF THE INVENTION

A preferred embodiment of a radiographic diagnosis apparatus according to the present invention will now be described with reference to the accompanying drawings.

First Embodiment (Arrangement of Radiographic Diagnosis Apparatus)

Figure 1:
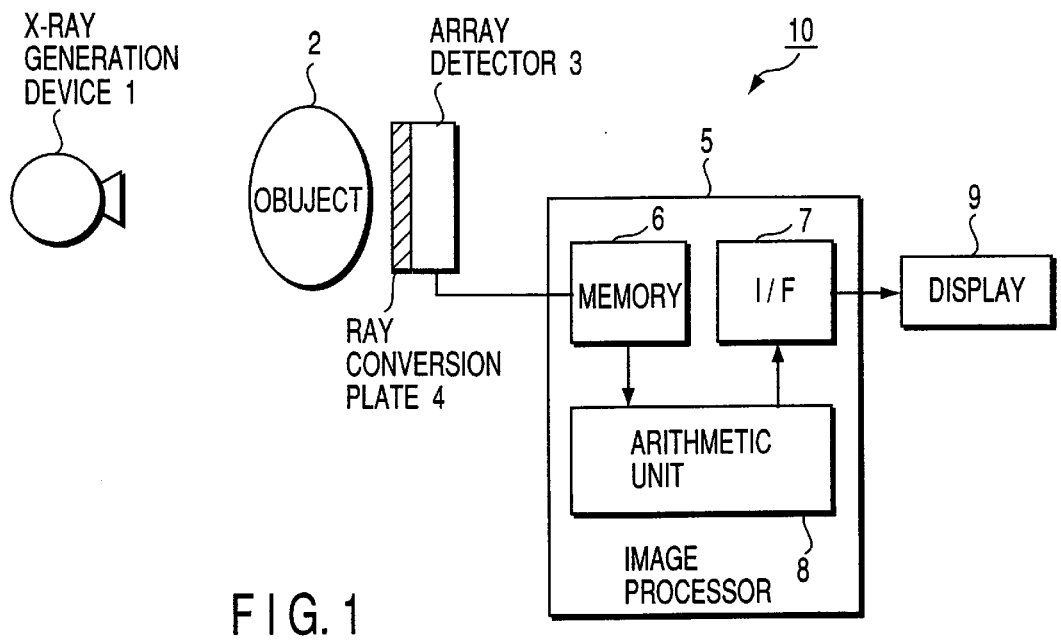
FIG. 1 is a schematic view showing the overall structure of the first embodiment of a radiographic diagnosis apparatus according to the present invention.

FIG. 1 is a block diagram showing the arrangement of the first embodiment of a radiographic diagnosis apparatus. Although this first embodiment will be explained by taking X-rays as an example of radiation, some other radiation can also be used. An X-ray diagnosis apparatus 10 includes an X-ray generation device 1, a two-dimensional array detector 3, a ray conversion plate 4, an image processor 5, and a display 9. The X-ray generation device 1 irradiates an object 2 with X-rays. The two-dimensional array detector 3 is formed by arraying small detecting elements in a two-dimensional matrix. This two-dimensional array detector 3 opposes the X-ray generation device 1 with the object 2 interposed between them, and detects X-rays transmitted through the object 2 in units of pixels. The ray conversion plate 4 is placed between the array detector 3 and the X-ray generation device 1, or is adhered to the radiation incident surface of the array detector 3, and changes the properties of X-rays in units of pixels. The image processor 5 performs image processing on the basis of data from the array detector 3 and generates a radiographic diagnosis image. The display 9 displays the image reconstructed by the image processor 5. A detector described in U.S. Pat. No. 4,672,454 explained in "BACKGROUND OF THE INVENTION" can be used as the two-dimensional array detector 3.

The properties of X-rays radiated from the X-ray generation device 1 and transmitted through the object 2 are changed via the ray conversion plate 4 on the front surface of the two-dimensional array detector 3. Assume that this ray conversion plate 4 changes the properties into two types. The array detector 3 detects the property-changed X-ray signal transmitted through the object in units of pixels. The array detector 3 converts the detected signal into a digital signal and transfers this digital signal to the image processor 5. The signal is stored in a memory 6 and subjected to image processing by an arithmetic circuit 8. After that, the processed signal is transferred to the display 9, such as a display device or a film imager, via an I/F 7, and is displayed as an image.

(Configurations of Array Detector 3 and Ray Conversion Plate 4)

Figure 2A:
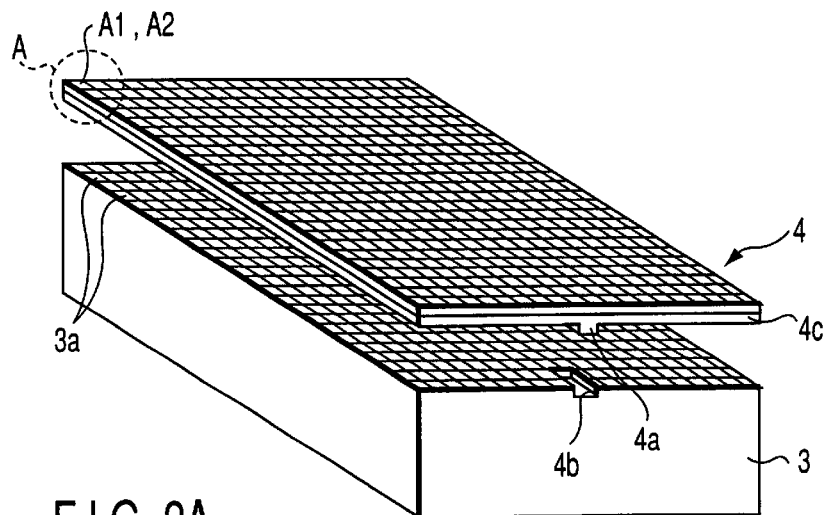
FIG. 2A is a perspective view of a ray conversion plate and an array detector according to the first embodiment.
Figure 2B:
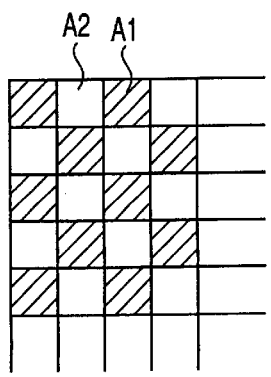
FIG. 2B is a plan view of the ray conversion plate.

The configurations of the array detector 3 and the ray conversion plate 4 will be described in detail below. FIG. 2A is a perspective view of the array detector 3 and the ray conversion plate 4. FIG. 2B is an enlarged plan view of a portion A indicated by the broken line in FIG. 2A.

The array detector 3 is formed by arraying, in a two-dimensional matrix (lattice), a large number of small detecting elements 3a for detecting X-rays generated from the X-ray generation device 1 (and transmitted through the object 2). Each detecting element 3a stores an electric charge corresponding to the incident X-ray dose and outputs it as an electrical signal.

The ray conversion plate 4 is formed by arraying, into a predetermined pattern, a plurality of (in this embodiment, two) different types of X-ray attenuating elements A1 and A2, for attenuating X-rays at different attenuation ratios, on a support plate 4c which hardly attenuates but transmits X-rays nearly 100%. In this embodiment, these attenuating elements A1 and A2 are two different types of metal elements having different atomic numbers and set to have a thickness by which, e.g., at least a 20% portion of 100-keV X-rays is transmitted. Each attenuating element A1 or A2 has the same pixel size as the detecting element 3a of the array detector 3. As shown in FIG. 2B, these attenuating elements A1 and A2 alternate in a checkerboard pattern.

The ray conversion plate 4 is overlapped on the array detector 3 with pixels of the two members aligned. For this alignment, projections 4a are formed on the four sides of the ray conversion plate 4, and recesses 4b are cut in corresponding portions of the array detector 3. In FIG. 2B, the support plate 4c of the ray conversion plate 4 and a support member of the array detector 3 are not shown. Also, the projection 4a and the recess 4b on only one of the four sides are illustrated for explanation. Since the recesses 4b and the projections 4a are so processed as to fit with no spacing between them, the relative position relationship between the ray conversion plate 4 and the array detector 3 does not change. Even when the ray conversion plate 4 is detached and attached, the positional relationship between the array detector 3 and the ray conversion plate 4 is always correct.

When the object 2 is irradiated with X-rays in this state, each pixel of the array detector 3 detects X-rays whose X-ray energy intensity is attenuated by either the X-ray attenuating element A1 or A2 of the ray conversion plate 4. Consequently, the detector 3 alternately outputs A1- and A2-attenuated X-ray signals.

(Operations of Array Detector 3 and Ray Conversion Plate 4)

Figure 3:
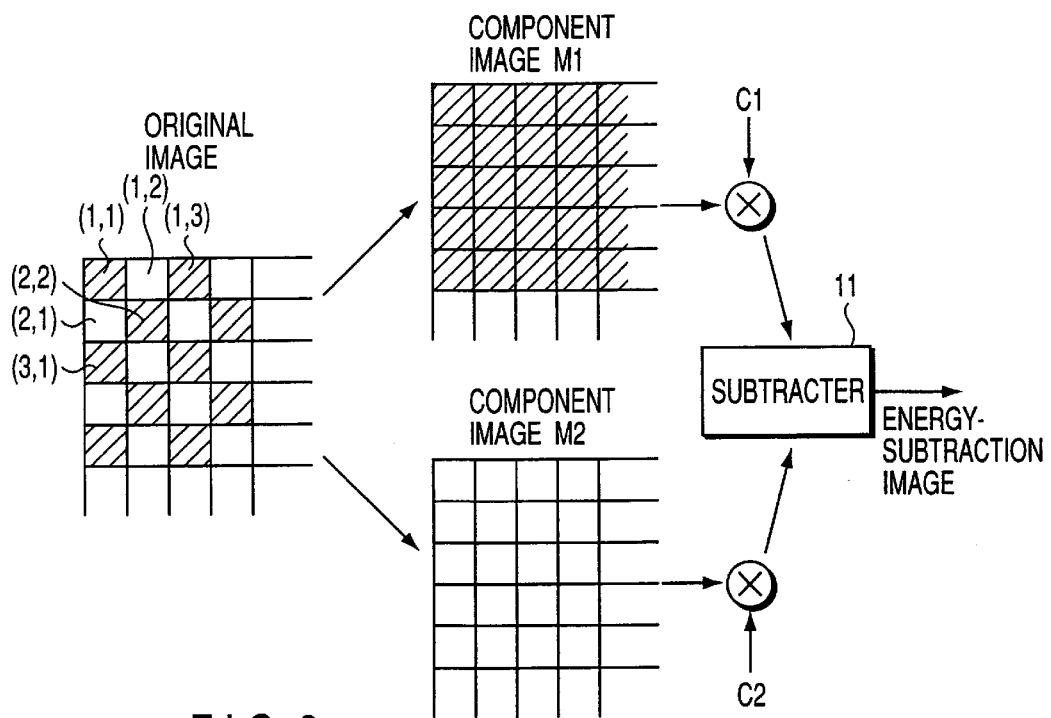
FIG. 3 is a view for explaining the procedure of image processing in the radiographic diagnosis apparatus according to the first embodiment.

The array detector 3 and the ray conversion plate 4 constructed as above operate in the following manner. FIG. 3 is a view schematically showing the pixel signal distribution on the array detector 3 and processing for the distribution.

On the array detector 3, pixels (hatched portions in FIG. 3) which detect X-rays attenuated through the X-ray attenuating elements A1 and pixels (blank portions in FIG. 3) which detect X-rays attenuated through the attenuating elements A2 are arranged in a checkerboard pattern (this image will be referred to as an original image hereinafter). From this original image, component images M1 and M2 are formed. The component image M1 is composed of only pixels which detect X-rays attenuated through the X-ray attenuating elements A1. The component image M2 is composed of only pixels which detect X-rays attenuated through the attenuating elements A2. Referring to FIG. 3, pixels (1,1), (1,3), ..., (2,2), ..., (3,1), ..., are pixels which detect X-rays attenuated through the X-ray attenuating elements A1. Pixels (1,2), (1,4), ..., (2,1), ..., (3,2), ..., are pixels which detect X-rays attenuated through the attenuating elements A2.

Each component image contains the number of pixels half that of the original image. Therefore, the number of pixels is made equal to that of the original image by allocating one pixel of the original image to two adjacent pixels. As an example, data of pixels (1,1), (1,1), (1,3), (1,3), ..., (2,2), (2,2), (2,4), (2,4), ..., on the original image are embedded in pixels (1,1), (1,2), (1,3), (1,4), ..., (2,1), (2,2), (2,3), (2,4), ..., respectively, on the component image M1, and data of pixels (1,2), (1,2), (1,4), (1,4), ..., (2,1), (2,1), (2,3), (2,3), ..., on the original image are embedded in pixels (1,1), (1,2), (1,3), (1,4), ..., (2,1), (2,2), (2,3), (2,4), ..., respectively, on the component image M2. This processing halves the spatial resolution in the horizontal direction. However, the component images M1 and M2 are formed by picking up only pixels transmitted through the X-ray attenuating elements A1 and A2, respectively.

This data embedding is not restricted to the above example. For instance, to make the horizontal and vertical resolutions equal to each other, it is possible to embed the average value of pixels (1,1) and (2,2) on the original image into four pixels (1,1), (1,2), (2,1), and (2,2) on the component image M1, and to embed the average value of pixels (1,2) and (2,1) on the original image into four pixels (1,1), (1,2), (2,1), and (2,2) on the component image M2.

After these component images M1 and M2 are formed as above, they are multiplied by predetermined coefficients C1 and C2, respectively, and subjected to arithmetic processing by a subtracter 11, thereby forming an energy-subtraction image or an image representing the energy absorption characteristic. That is, the values of individual pixels of the component images M1 and M2 are substituted into the equation $Y=C1 \times M1 + C2 \times M2$, and a linear arithmetic operation is performed to construct an image Y. Note that the coefficients C1 and C2 can be determined on the basis of any conventionally known method.

One suitable example will be described below. In this example, the ray conversion plate 4 is formed by using the X-ray attenuating elements A1 made of copper and having a thickness of 0.3 mm and the attenuating elements A2 made of aluminum and having a thickness of 3 mm. Assuming a human lung produces X-ray attenuation substantially equivalent to 10 cm of water, if a 1-cm thick rib exists in this lung, the array detector 3 detects the following signal. Note that the values described below are relative values when the lung on the component image M1 is 1.0.

(i) Signals (on the component image M1) obtained by detecting X-rays attenuated through the X-ray attenuating element A1
Lung: 1.00
Rib: 0.80

(ii) Signals (on the composition image M2) formed by detecting X-rays attenuated through the attenuating element A2
Lung: 0.78
Rib: 0.64

Accordingly, to erase the shadow of the rib by energy subtraction, the component image M2 is multiplied by 0.80/0.64(=1.25), and the product is subtracted from the component image M1. Consequently, a signal having a component of 1−0.78×1.25(=0.025) remains in the lung, so the shadow of only the lung is displayed on an image from which the rib is eliminated. In this example, energy subtraction is described by:

$$Y = 1 \times M1 - 1.25 \times M2$$

That is, the coefficients C1 and C2 are set such that C1=1 and C2=−1.25. Since these coefficients are determined by the tube voltage of the X-ray generation device 1, they are previously calculated in accordance with the tube voltage used. Note that if the X-ray attenuating elements A1 and A2 absorb X-rays too much, only little X-rays enter the array detector 3, and this lowers the S/N ratio. Therefore, the materials of the attenuating elements A1 and A2 must be carefully chosen.

In the first embodiment as described above, radiation generated from a radiation source is passed through a plurality of attenuating elements constructing a plate-like member. This radiation is attenuated at predetermined ratios and converted into a plurality of different types of energy radiations. These different types of radiations are detected by detecting elements placed in positions corresponding to the attenuating elements. Consequently, in a radiographic diagnosis apparatus using a two-dimensional array detector, it is possible to prevent an artifact resulting from the motion of an object, or by the shadow of an internal structure of the detector, without deteriorating the S/N ratio, thereby simultaneously obtaining images of the object by using radiations differing in energy.

Other embodiments of the present invention will be described below. In the following embodiments, the same reference numerals as in the first embodiment denote the corresponding parts, and a detailed description thereof will be omitted.

Second Embodiment

Figure 4:
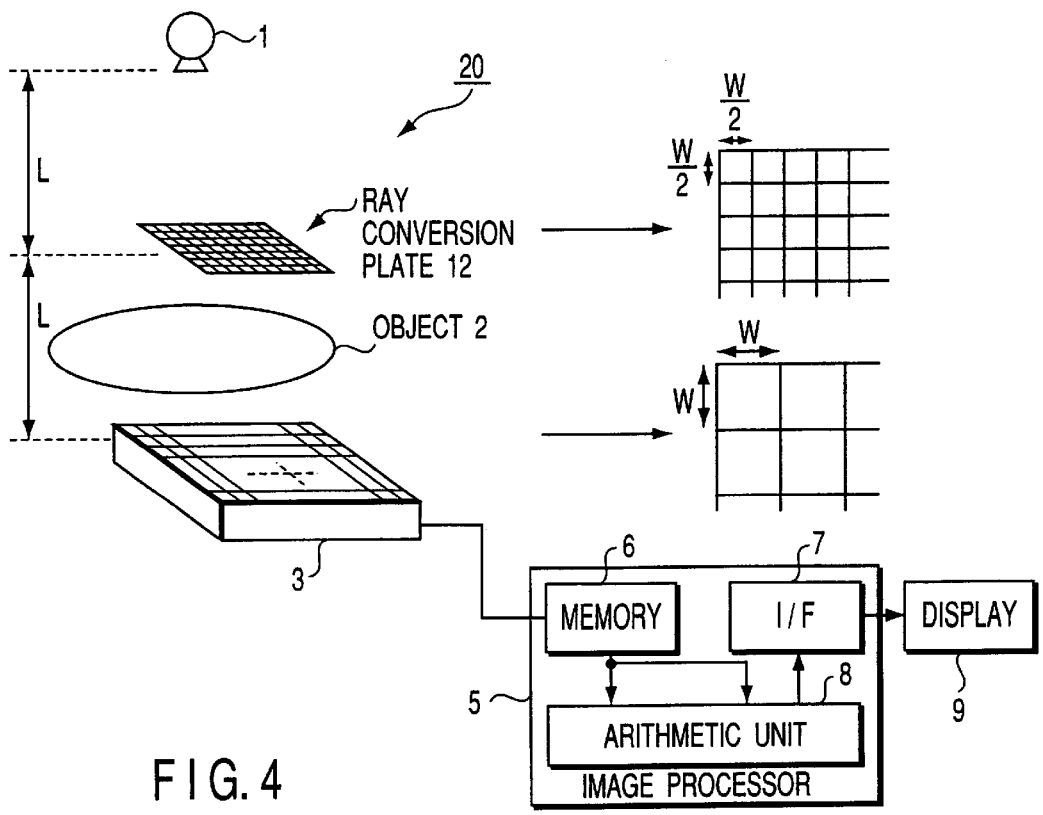
FIG. 4 is a view schematically showing the overall structure of the second embodiment of a radiographic diagnosis apparatus according to the present invention.

FIG. 4 shows an X-ray diagnosis apparatus 20 according to the second embodiment. In this second embodiment, a ray conversion plate 12 is placed between the object 2 and the X-ray generation device 1. Since, therefore, X-rays are attenuated before irradiating the object 2, the dose of the radiation to the object 2 can be reduced compared to the first embodiment. However, the ray conversion plate 12 and the array detector 3 must be aligned (so that X-rays passing through attenuating elements correctly enter the corresponding detecting elements).

Additionally, each detecting element of the array detector 3 is so placed as to have an area substantially equal to an X-ray irradiation area when radiation passing through the corresponding detecting element is applied to the array detector 3. More specifically, the ray conversion plate 12 is placed in the middle of the distance between the X-ray generation device 1 and the array detector 3. Also, the length and width (the length of one side of a square) of each attenuating element of the ray conversion plate 12 are one-half of those (the length of one side of a square) of each detecting element of the array detector 3. That is, each attenuating element of the ray conversion plate 12 is projected onto the corresponding detecting element of the array detector 3 after being magnified at four times.

Note that this magnification further increases when the size of each attenuating element of the ray conversion plate 12 is decreased compared to that of the detecting element of the array detector 3, so the ray conversion plate 12 can be placed nearer to the X-ray generation device 1. However, the penumbra is produced on the array detector 3 by the thickness of the metal of the attenuating element. This significantly deteriorates the spatial resolution on the edges of an image. That is, the magnification has its limit. Under geometric conditions in actual image sensing, four times is presumably the limit of the magnification when the thickness of the metal element is 3 mm. Consequently, the attenuating element size of the ray conversion plate 12 must be so designed as to meet a magnification of four times or less. So, the length of one side of the attenuating element is half that of the detecting element or less.

Third Embodiment

FIG. 5 schematically shows an X-ray diagnosis apparatus 30 according to the third embodiment. In this third embodiment, as in the second embodiment, a ray conversion plate 15 is placed between the object 2 and the X-ray generation device 1 and achieves the same effect as in the first embodiment while reducing the exposure of the object 2 to radiation. However, the relative position of the ray conversion plate 15 with respect to the array detector 3 need not be precisely fixed, unlike in the second embodiment.

That is, X-ray blocking elements 13 for blocking X-rays at a predetermined ratio are formed, instead of attenuating elements, on the edges of the four sides of the ray conversion plate 15 according to this embodiment. The array detector 3 detects the positions (blocking positions) of these X-ray blocking elements 13, thereby detecting the relative position of the ray conversion plate 15 with respect to the array detector 3 and correcting any positional deviation by signal processing. Although FIG. 5 shows only blocking elements formed on the upper and left-hand edges, blocking elements are also formed in corresponding portions on the lower and right-hand edges.

More specifically, in this embodiment the ray conversion plate 15 is placed in a location (in the middle of the distance from the X-ray generation device 1 to the array detector 3) where the magnification is four times, as in the second embodiment. However, each attenuating element of the ray conversion plate 15 has the same size as the detecting element of the array detector 3. The number of the attenuating elements of the ray conversion plate 15 is one fourth of that of the detecting elements of the array detector 3 if the array detector 3 exactly covers the irradiation area of the X-ray. However, in the actual product, the number of the attenuating elements of the ray conversion plate 15 is more than one fourth of that of the detecting elements of the array detector 3 in order to sufficiently covers the irradiation area of the X-ray by the array detector 3.

As the X-ray blocking element 13, a material such as lead having very large X-ray absorption is used. For example, when lead with a thickness of 2 mm is placed, X-rays behind this lead are attenuated to 0.1% or less. So, lead is well usable as a blocking material. Note that the position of a blocking material can be well estimated if an X-ray attenuation of 95% or more is performed. Therefore, a material by which X-ray transmission is 5% or less can be suitably used as a blocking material.

In the X-ray diagnosis apparatus 30 with the above arrangement, any positional deviation of the ray conversion plate 15 from the array detector 3 is detected by the following operation. Assume that the ray conversion plate 15 deviates from the array detector 3 as shown in FIG. 6.

The detecting elements of the array detector 3 and the attenuating elements of the ray conversion plate 15 have the same size, and the magnification is four times (two times in the horizontal direction and two times in the vertical direction). Therefore, whatever positional deviation takes place, a state in which the shadows (black solid portions) of the X-ray blocking elements 13 completely cover the detecting elements on the array detector 3 necessarily exists. FIG. 6 also shows a profile of the (k+1)th line on the array detector 3. As shown in FIG. 6, pixels in the (i+1)th column are completely covered with the shadow of the X-ray blocking element 13. Pixels in the (i+2)th column slightly contain the shadow of the X-ray blocking element 13. FIG. 6 also reveals that the shadow of the second X-ray blocking element 13 is produced in the (i+5)th column at an interval of 3 pixels.

That is, when the X-ray blocking element 13 is a substance which completely blocks X-rays, pixels in the (i+1)th and (i+5)th columns produce pixel signals corresponding to scattering ray components generated from the object 2. A pixel adjacent to a blocked pixel in the horizontal direction always has a larger pixel value than that of the blocked pixel.

In other words, a pixel completely covered with the X-ray blocking element 13 gives a minimum value in a local area including the target pixel. The local area can be determined beforehand based on the situation of radiography. Accordingly, after image acquisition, an image processor 5 calculates a minimum value of the acquired images in the local area. If a value close to this value is present at an interval of four pixels, pixels (in the (i+1)th and (i+5)th columns in FIG. 6) which give this minimum value are pixels corresponding to the position of the X-ray blocking element 13 on the ray conversion plate 15.

As shown in FIG. 6, the (i+1)th column ((i+5)th column) is completely covered with the shadow of the X-ray blocking element 13. Therefore, the pixel value is a scattering ray component S coming from the perimeter. In contrast, pixels in the adjacent i-th column ((i+4)th column) and (i+2)th column ((i+6)th column) are partially covered with the shadow of the X-ray blocking element 13. Hence, letting a and (1−a) be the ratios of regions covered with the shadow of the X-ray blocking element 13 to the whole area of pixels in the i-th column ((i+4)th column) and the (i+2)th column ((i+6)th column), and letting E be the value of pixels which are not at all covered with the X-ray blocking element 13, a pixel value E1 of the i-th column ((i+4)th column) and a pixel value E2 of the (i+2)th column ((i+6)th column) are represented by:

$E1$ (the pixel value of the $i$-th column)$=E \times a + S$ $E2$ (the pixel value of the $(i+2)th$ column)$=E \times (1-a) + S$ From the above equations, the pixel value E when a pixel is not at all covered with the X-ray blocking element 13 is given by:

$E = (E1 + E2) - 2 \times S$

That is, a twofold value of the pixel value S of the (i+1)th column is subtracted from the sum of the pixel values E1 and E2 of the i-th and (i+2)th columns. Accordingly, a is given by:

$a = (E1 - S)/E$

The above example is the detection of positional deviation based on the blocking elements 13 formed on the upper edge. This positional deviation detection is also similarly performed on the basis of the blocking elements 13 formed on the lower edge. That is, the positional deviations of the uppermost line and the lowest line are obtained by these detection. The positional deviations of intermediate lines are obtained by interpolating the results of the two detections.

By the above operation, the ratio a of the region covered with the X-ray blocking element 13 to the whole area of the pixels is calculated. The horizontal positional deviation between the ray conversion plate 15 and the array detector 3 can be estimated by calculations to be a times the width of one pixel of the array detector 3.

When the positional deviation of the ray conversion plate 15 is detected, the horizontal positional deviation of each horizontal line can be known by a linear arithmetic operation. Therefore, the ratios a and (1−a) at which pixels are covered with X-ray attenuating elements A1 and attenuating elements A2 can be obtained for all pixels.

A component image M1 can be estimated from an original image by using a.

Figure 7:
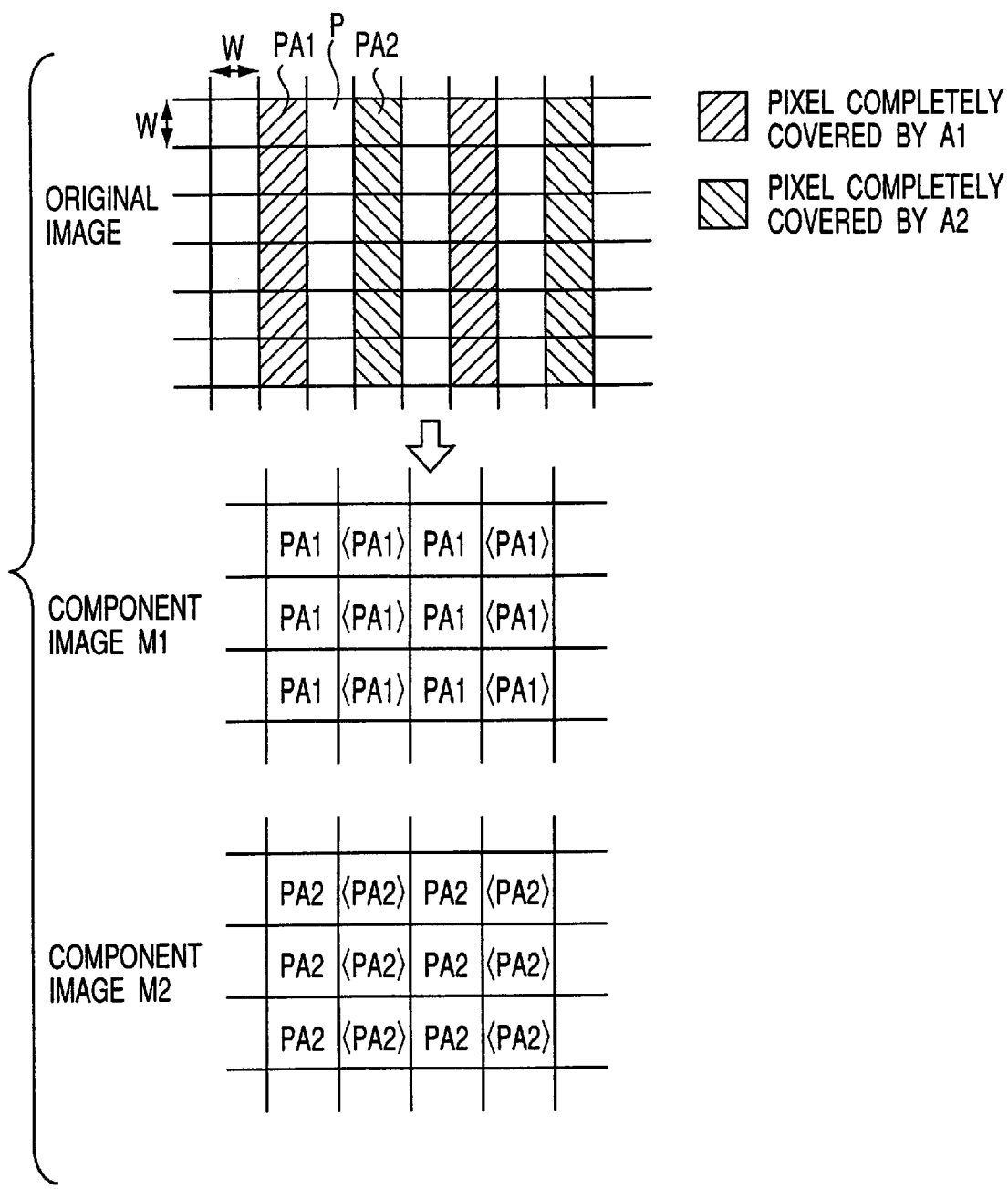
FIG. 7 is a view showing a method of obtaining component images of different energies from an original image obtained by the detector in the radiographic diagnosis apparatus according to the third embodiment.

Let P be the pixel value of a pixel of the array detector 3 when the ray conversion plate 15 is absent. For the sake of convenience of explanation, assume that the attenuating elements A1 and A2 of the ray conversion plate 15 are alternately arrayed into the form of stripes, not a checkerboard pattern. As shown in FIG. 7, letting PA1 be the pixel value of pixels completely covered with the X-ray attenuating elements A1 and PA2 be the pixel value of pixels completely covered with the attenuating elements A2, we have:

$P = PA1 \times a + PA2 \times (1-a)$

PA2 of a pixel can be estimated from observed values of pixels surrounding the pixel of interest and completely covered with the attenuating elements A2. Hence, if a pixel whose P is observed is completely covered with the X-ray attenuating element A1, the estimated value is <PA1> given by:

$<PA1> = (P - PA2 \times (1-a))/a$

The component image M1 can be estimated from PA1 and <PA1>. Analogously, the component image M2 can be estimated from PA2 and <PA2>, the latter of which is given by:

$<PA2> = (P - PA1 \times a)/(1-a)$

In this manner, the component images M1 and M2 that compensate for any positional deviation of the ray conversion plate 15 from the array detector 3 are obtained. By using these component images M1 and M2, a method such as energy subtraction can be applied in the same way as in the first embodiment.

Although horizontal positional deviation has been described above, vertical positional deviation can also be obtained in a similar manner.

Also, even when the metal elements of the ray conversion plate are arrayed in a checkerboard pattern as shown in FIG. 2B, the positions of pixels on the array detector which are completely covered with the X-ray attenuating elements A1 and A2 can be known by accurately detecting the positions of the X-ray blocking elements on the upper, lower, right-hand, and left-hand sides described above. Additionally, the component images M1 and M2 can be formed by obtaining for each pixel the ratio a at which the pixel is covered with the X-ray attenuating element A1.

Fourth Embodiment

Figure 8:
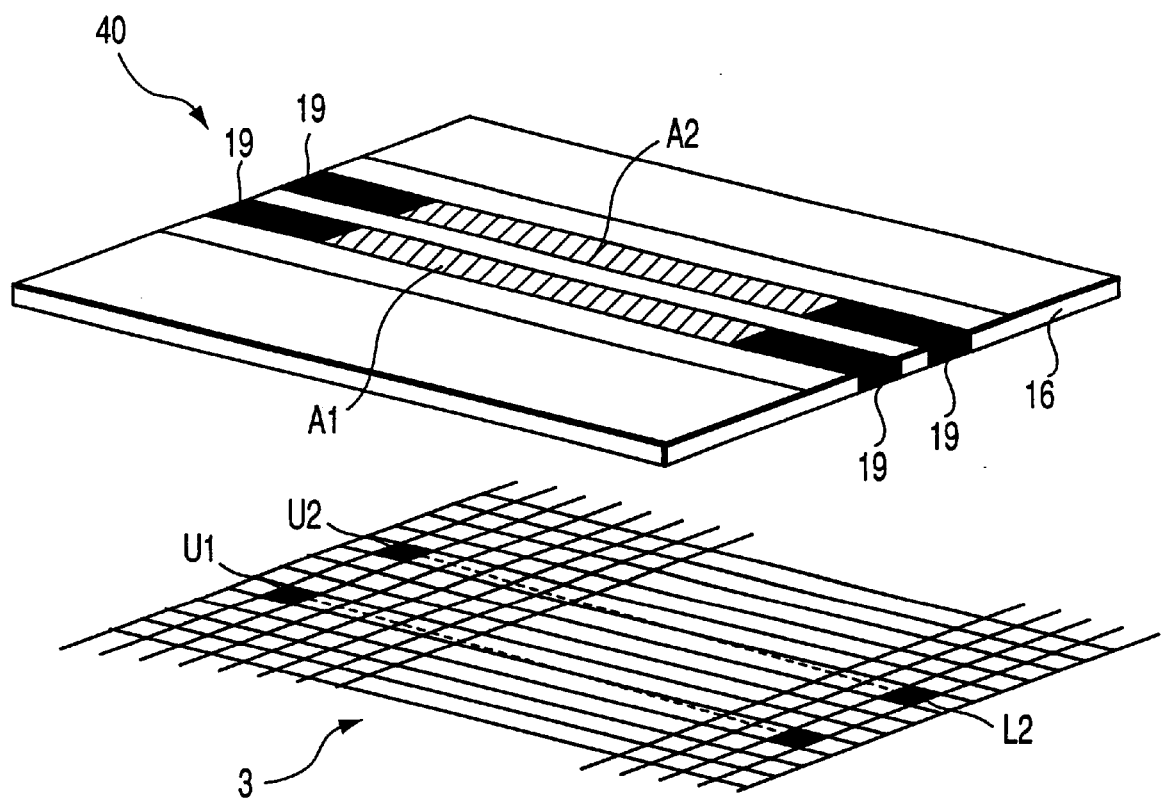
FIG. 8 is a perspective view showing the overall structure of the fourth embodiment of a radiographic diagnosis apparatus according to the present invention.

FIG. 8 is a perspective view showing a ray conversion plate 16 and the array detector 3 as main parts of an X-ray diagnosis apparatus 40 according to the fourth embodiment. Referring to FIG. 8, the ray conversion plate 16 according to this embodiment is an example of the simplest ray conversion plate. Although FIG. 8 shows only a part of the ray conversion plate 16, X-ray attenuating elements A1 and A2 are alternately arrayed in every other column, and X-ray blocking elements 19 are formed in four portions at the ends of two attenuating elements A1. This ray conversion plate 16 can be interposed between an X-ray generation device and an object as in the second and third embodiments, or attached to the surface of the array detector as in the first embodiment. The width of the columns of the X-ray attenuating elements A1 and A2 is the same as that of the array detector 3 if the ray conversion plate 16 is placed between the X-ray generation device 1 and the object 2 as in the third embodiment. The width of the columns of the X-ray attenuating elements A1 and A2 is twice as that of the array detector 3 if the ray conversion plate 16 is placed on the array detector 3 as in the first embodiment.

The image processor 5 detects positions U1, U2, L1, and L2 of pixels on the array detector 3 which are completely covered with the shadows of the X-ray blocking elements 19. After that, the image processor 5 determines that all pixels positioned on a line connecting U1 and L1 are completely covered with the X-ray attenuating element A1. Likewise, the image processor 5 determines that all pixels positioned on a line connecting U2 and L2 are completely covered with the X-ray attenuating element A1. The image processor 5 also determines that pixels on a line intermediate between these two lines are covered with the X-ray attenuating element A2.

When the positions of pixels on the array detector 3 that are completely covered with the X-ray attenuating elements A1 and A2 are thus determined, component images M1 and M2 can be formed by using these pixels, since it is assumed that the pitch of the X-ray attenuating elements A1 (or A2) is four times the pitch of the detecting element columns of the array detector and pixels corresponding to A1 and A2 are determined by the period of four pixels in detecting element columns which correspond to attenuating element lines.

Fifth Embodiment

Figure 9:
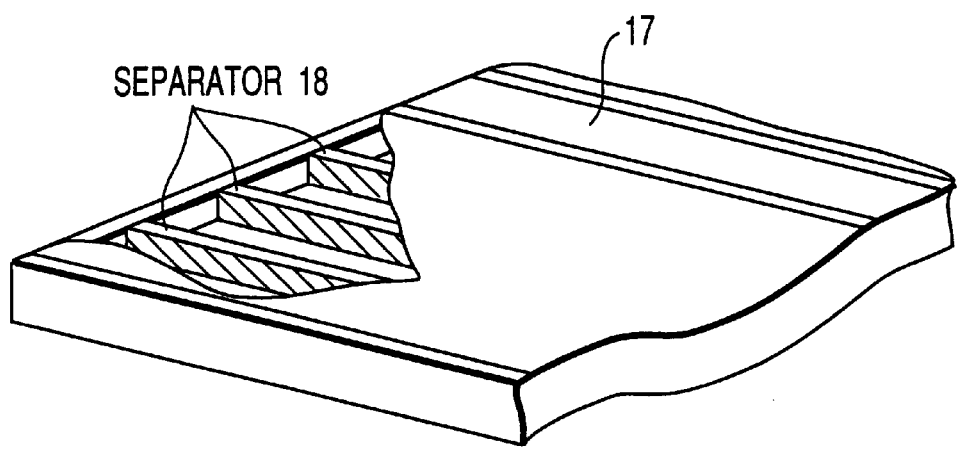
FIG. 9 is a partially exploded perspective view showing a ray conversion plate of the fifth embodiment of a radiographic diagnosis apparatus according to the present invention.

FIG. 9 is a partially exploded perspective view showing a ray conversion plate 17 according to this embodiment. This ray inversion plate 17 is characterized by having a function of changing the properties of X-rays, when the image data is acquired with the ray inversion plate 17 attached to the surface of the array detector 3, and also having a function of a grid for removing rays scattered by the object 2. That is, in the ray conversion plate 17 attenuating elements constructing it are separated by separators 18 which attenuate X-rays at a predetermined ratio.

More specifically, the separators 18 that are thin plate members made of a material such as lead having large X-ray absorption are present between the metal elements (attenuating elements) of the ray conversion plate 17. These separators 18 absorb scattering ray components incident on the ray conversion plate 17 and thereby reduce scattering to the ambient environment. In FIG. 9, the attenuating elements form lines in the vertical direction, and the separators 18 extend in the vertical direction. However, it is also possible to enhance the scattering ray reducing function by forming separators in both the vertical and horizontal directions in a lattice-like pattern.

The positions of the detecting elements of the array detector 3 and the positions of the attenuating elements of the ray conversion plate 17 can be aligned by the method as described in the first embodiment. So, the scattering ray preventing separators can be formed above the boundaries of the detecting elements on the array detector 3. This minimizes reduction in the direct X-ray component attributed to the separators. Note that the separators cannot well reduce scattering rays unless the thickness and the material are such that at least 80% of 100-keV X-rays are transmitted. Therefore, the thickness must be about 20 μm or more when lead is used.

The present invention is not limited to the above embodiments and can be practiced in the form of various modifications. That is, practical examples such as the arrangement of the ray conversion plate in each embodiment, the relative size with respect to the array detector, and the image processing by the image processor are merely examples. So, the present invention is not restricted to these examples.

According to the present invention as has been described above, in a radiographic diagnosis apparatus which acquires image data based on radiations differing in energy by using a two-dimensional array detector, it is possible to prevent an artifact caused by the motion of an object, or by the shadow of an internal structure of the detector, without deteriorating the S/N ratio. That is, it is possible to provide an image representing energy subtraction or an X-ray absorption characteristic by using a ray conversion plate, and to enhance the X-ray diagnosis capability using an array detector.

What is claimed is:

1. A radiographic apparatus comprising:
    a radiation source configured to irradiate an object with radiation;
    a detector comprising a plurality of detecting elements configured to detect the radiation generated by said radiation source and transmitted through the object; and
    a ray conversion plate detachably attached to the detection surface of the detector and comprising a plurality of different types of attenuating elements for attenuating radiation at different attenuation ratios,
    wherein radiations differing in energy attenuated by said plurality of different types of attenuating elements are detected by said detecting elements respectively corresponding to said attenuating elements and each of said detecting elements and each of said attenuating elements have substantially equal areas.

2. The apparatus according to claim 1, wherein said attenuating elements of said ray conversion plate are separated by separators which attenuate the radiation at a predetermined ratio.

3. The apparatus according to claim 1, wherein said ray conversion plate comprises a projection and said detector comprises a recess to which the projection is fixed.

4. A radiographic apparatus comprising:
    a radiation source configured to irradiate an object with radiation;
    a detector comprising a plurality of detecting elements configured to detect the radiation generated by said radiation source and transmitted through the object; and
    a ray conversion plate placed between said radiation source and the object and comprising a plurality of different types of attenuating elements for attenuating radiation at different attenuation ratios,
    wherein radiation differing in energy attenuated by said plurality of different types of attenuating elements are detected by said detecting elements respectively corresponding to said attenuating elements and each of said detecting elements and each of said attenuating elements has an area substantially equal to an irradiation area of radiation, passing through each of said attenuating elements, on a detection surface of said detector.

5. The apparatus according to claim 4, wherein said ray conversion plate comprises a blocking element, for blocking the radiation at a predetermined ratio, in a predetermined position, and said detector detects a position of said blocking element on the basis of an incident amount of radiation, thereby detecting a relative position of said ray conversion plate with respect to said detector.

6. The apparatus according to claim 5, further comprising means for correcting each of radiation images differing in energy in accordance with the relative position of said ray conversion plate detected by said detector.

7. The apparatus according to claim 4, wherein said attenuating elements of said ray conversion plate are separated by separators which attenuate the radiation at a predetermined ratio.

8. A radiographic diagnosis method comprising:
    emitting radiation forward an object;
    irradiating a ray conversion plate with the radiation, said ray conversion plate being placed between said radiation source and the object and comprising a plurality of different types of attenuating elements for attenuating radiation at different attenuation ratios;
    detecting radiations with a plurality of energies transmitted through said ray conversion plate by a detector comprising a plurality of detecting elements;
    detecting a positional misalignment of the attenuating elements and the detecting elements; and
    correcting the positional misalignment to obtain radiation images with a plurality of energies based on the detected radiations.

9. A plate member which is placed on a detection surface of a detector formed by two-dimensionally arraying detecting elements, and which changes properties of radiation, the plate member comprising:
    at least two types of radiation attenuating substances having different atomic numbers two-dimensionally alternately arrayed on a support plate,
    the width of each substance is 0.5 W to 1 W of a width W of said detecting element,
    a thickness of each substance is selected to transmit at least 20% of 100-keV radiation;
    a support member for supporting said attenuating substance at edges thereof; and a plurality of fitting members provided on the support member for fitting with and fixing said plate member on the detector.

10. The member according to claim 9, further comprising at least two radiation blocking substances which are arranged, in one direction of an array of said detecting elements, on an edge at an interval of twice the width of said radiation attenuating substance, and which attenuate not less than 95% of 100-keV radiation, the width of said radiation blocking substance being twice the width of said attenuating substance.

11. The member according to claim 9, in which said plurality of different types of radiation attenuating substances are arrayed in a checkerboard pattern.

12. The member according to claim 9, in which said plurality of different types of radiation attenuating substances are arrayed into a form of stripes.

13. The apparatus according to claim 9, wherein said attenuating elements of said ray conversion plate are separated by separators which attenuate the radiation at a predetermined ratio.

14. A position detection method of detecting positional deviation between a radiation adjusting member and a detector comprising a plurality of detecting elements two-dimensionally arrayed in a matrix, said radiation adjusting member being placed between a radiation source and said detector, comprising at least two radiation blocking elements formed in one direction of array directions of said detecting elements, and made from at least two types of attenuating substances which attenuate radiation at predetermined attenuation ratios, in which each of said radiation blocking elements is irradiated at a magnification of two times in longitudinal and lateral directions when forming an image on said detector, thereby forming a shadow, having a width twice the width of said detecting element, on said detector, and said radiation blocking elements are geometrically arranged to make an interval between one radiation blocking element and a next radiation blocking element twice the width of said detecting element, the method comprising:

obtaining a pixel which gives a minimum pixel value L1 among pixels positioned in a region near images formed by said radiation blocking elements; and detecting positional deviation between said detector and said radiation adjusting member based on differences L1–L2 and L1–L3 between pixel values L2 and L3 of two pixels, adjacent in the one direction to said pixel which gives the minimum pixel value, and the minimum pixel value L1.

15. The method according to claim 14, in which at least two further radiation blocking elements are provided in another direction of the array directions of said detecting elements, and which further comprises:

detecting positional deviation between said detector and said radiation adjusting member based on differences L1–L4 and L1–L5 between pixel values L4 and L5 of two pixels, adjacent in the other direction to said pixel which gives the minimum pixel value, and the minimum pixel value L1.

16. A radiographic apparatus comprising:

a radiation source for emitting radiation toward an object;

a detector opposing said radiation source with the object interposed therebetween and comprising detecting elements arrayed in a lattice-like pattern to detect radiation transmitted through the object and to output data;

a ray conversion plate detachably attached to a detection surface of said detector and formed by arraying, into a predetermined pattern, a plurality of different types of attenuating materials which attenuate the radiation emitted from the radiation source at different predetermined ratios, and wherein said detector detects radiations different in properties attenuated by said ray conversion plate, thereby forming images corresponding to the attenuation ratios of said attenuating materials and said detecting element and said attenuating material have substantially equal areas.

17. The apparatus according to claim 16, wherein said plurality of different types of attenuating materials are separated by plate members for attenuating radiation at a predetermined ratio.

18. The apparatus according to claim 16, wherein said attenuating elements of said ray conversion plate are separated by separators which attenuate the radiation at a predetermined ratio.

19. The apparatus according to claim 16, wherein said ray conversion plate comprises a projection and said detector comprises a recess to which the projection is fixed.

20. A radiographic diagnostic apparatus comprising:

a radiation source for emitting radiation toward an object;

a detector opposing said radiation source with the object interposed therebetween and comprising detecting elements arrayed in a lattice-like pattern to detect radiation transmitted through the object and to output data; and a ray conversion member placed between said radiation source and the object and formed by arraying, into a predetermined pattern, a plurality of different types of attenuating materials which attenuate the radiation emitted from the radiation source at different predetermined ratios, and wherein said detector detects radiations different in properties attenuated by said ray conversion plate, thereby forming images corresponding to the attenuation ratios of said attenuating materials and said detecting elements have areas substantially equal to irradiation areas when the radiations, passing through said attenuating materials respectively corresponding to said detecting elements, have reached said detector.

21. The apparatus according to claim 20, wherein a blocking element for blocking radiation at a predetermined ratio is formed in a predetermined position of said ray conversion plate, and said detecting element detects a portion blocked by said blocking element, thereby detecting a relative position of said ray conversion plate with respect to said detector.

22. The apparatus according to claim 21, further comprising means for correcting each of radiation images differing in energy in accordance with the relative position of said ray conversion plate detected by said detector.

23. The apparatus according to claim 20, wherein said plurality of different types of attenuating materials are separated by plate members for attenuating radiation at a predetermined ratio.

24. A radiographic diagnosis method of irradiating an object with radiation by using a radiation source, and forming an image by detecting the radiation transmitted through the object by using a detector opposing said radiation source with the object interposed therebetween, in which a ray conversion plate is placed between said radiation source and said object, said ray conversion plate being formed by arraying a plurality of different types of substances which transmit radiation while changing properties thereof and comprising two radiation blocking members arranged at a predetermined interval, and the method comprising:

detecting a relative position of said ray conversion plate with respect to said detector by detecting positions of said blocking elements on said detector; and correcting outputs from said detecting elements of said detector in accordance with the detected relative position, thereby forming an image for each radiation transmitted through said plurality of different types of substances of said ray conversion plate.

* * * * *